United States Patent [19]

Peter et al.

[11] Patent Number: 5,185,368

[45] Date of Patent: Feb. 9, 1993

[54] POLYETHYLENE GLYCOL CARBAMATES

[75] Inventors: Heinrich Peter, Binningen; Theophile Moerker, Füllinsdorf, both of Switzerland

[73] Assignee: Ciba-Geigy Corporation, Ardsley, N.Y.

[21] Appl. No.: 221,860

[22] Filed: Jul. 20, 1988

[30] Foreign Application Priority Data

Jul. 23, 1987 [CH] Switzerland .......................... 2794/87

[51] Int. Cl.$^5$ ............................................. A61K 31/00
[52] U.S. Cl. .................................. 514/476; 514/507;
514/517; 556/45; 556/138; 556/1; 558/50;
558/262; 560/13; 560/16; 560/29; 560/148;
560/159; 560/169
[58] Field of Search ................. 560/159, 169, 148, 29,
560/13, 16; 260/404.5; 548/341; 558/50, 262;
514/476, 507, 517

[56] References Cited

U.S. PATENT DOCUMENTS

| | | | |
|---|---|---|---|
| 3,634,407 | 1/1972 | Gaemnann | 260/239.3 |
| 4,419,365 | 12/1983 | McLachlan | 424/320 |
| 4,612,122 | 9/1986 | Ambrus et al. | 210/638 |
| 4,671,901 | 6/1987 | Green | 260/404.5 |
| 4,684,482 | 8/1987 | Green | 260/404.5 R |
| 4,764,523 | 8/1988 | Heinrich | 514/18 |
| 4,954,634 | 9/1990 | Heinrich et al. | 560/159 |

FOREIGN PATENT DOCUMENTS 1163337  2/1964  Fed. Rep. of Germany .

OTHER PUBLICATIONS

Helv. Chim. Acta. vol. 46 pp. 1385-1389 (1963).

Merck Index 10th ed p. 412 Item #2839 (1983).

*Primary Examiner*—Michael L. Shippen
*Attorney, Agent, or Firm*—Irving M. Fishman; Karen G. Kaiser

[57] ABSTRACT

Compounds of the formula

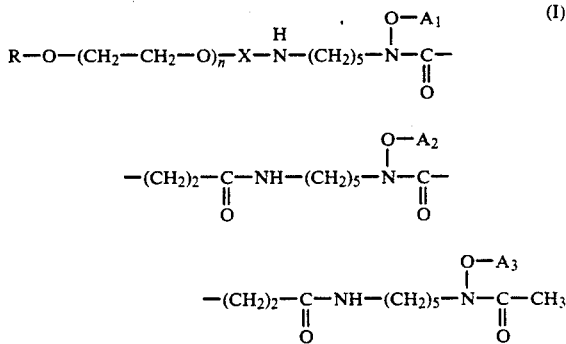

in which R is alkyl having up to 4 carbon atoms, n has an average value of at least 9, X is a radical of the formula $-C(=O)-(NH-SO_2)_m-$ in which m is 0 or 1 and, if m is 1, the carbonyl group may be bonded to the oxygen atom or to the nitrogen atom, and each of the radicals $A_1$, $A_2$ and $A_3$, independently of the others, is hydrogen or an acyl radical, and salts of salt-forming compounds of formula I, as well as metal complexes of compounds of formula I, in which $A_1$, $A_2$ and $A_3$, are hydrogen can be used as metal chelators and as auxiliaries in diagnosis.

11 Claims, No Drawings

POLYETHYLENE GLYCOL CARBAMATES

The invention relates to polyethylene glycol carbamates, especially corresponding derivatives of desferrioxamine compounds and metal complexes thereof, more especially compounds of the formula

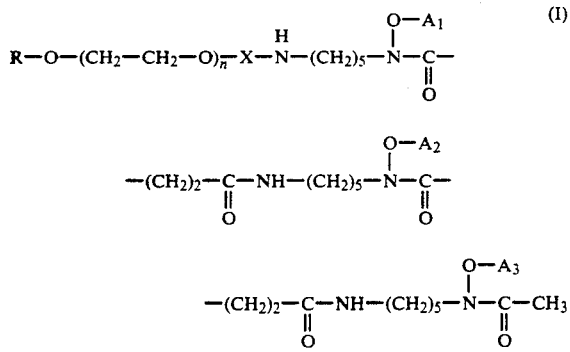

in which R is alkyl having up to 4 carbon atoms, n has an average value of at least 9, X is a radical of formula $-C(=O)-(NH-SO_2)_m-$ in which m is 0 or 1 and, if m is 1, the carbonyl group may be bonded to the oxygen atom or to the nitrogen atom, and each of the radicals $A_1$, $A_2$ and $A_3$, independently of the others, is hydrogen or an acyl radical, and salts of salt-forming compounds of formula I, as well as metal complexes of compounds of formula I, in which $A_1$, $A_2$ and $A_3$ represent hydrogen, and also to processes for the manufacture of such compounds, to forms of administration containing them, such as pharmaceutical and diagnostic forms of administration, and to their use for therapeutic and diagnostic purposes.

Desferrioxamine B (H. Bickel et al., Helv. Chim. Acta, Vol. 46, page 1385 [1963]) of the formula

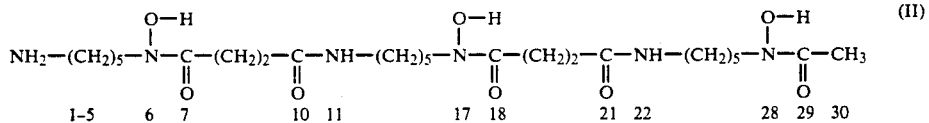

is designated, in accordance with rule C-06 (replacement nomenclature) of the official IUPAC nomenclature, by the systematic name 6,17,28-trihydroxy-7,10,18,21,29-pentaoxo-6,11,17,22,28-pentaazatriacontylamine. For the sake of simplicity, however, hereinafter the names of the compounds of the present invention are derived from the trivial name, the position of individual acyl radicals in each case being related to the nitrogen atom, designated N, of the amino group in the 1-position, or to the oxygen atoms, designated 0, 0' and 0", of the hydroxy groups in positions 6, 17 and 28, respectively.

One of the properties of desferrioxamine B and its addition salts is the ability to form stable chelate-like metal complexes, especially with trivalent metal ions, such as chromium(III), aluminium and especially iron-(III) ions. Used accordingly, desferrioxamine B can prevent the deposit of iron-containing pigments in tissue and, where there are existing deposits of iron in the organism, for example in the case of haemochromatosis, haemosiderosis, cirrhosis of the liver and poisoning with compounds of trivalent iron, can cause excretion of the iron. The therapeutic use of desferrioxamine B and its salts, for example the methanesulfonate, therefore extends generally to pathological conditions that are associated with excessive loading of the organism with iron(III) ions, such as thalassaemia major, sickle cell anaemia, sideroachrestic anaemia, aplastic anaemia and other forms of anaemia in which haemosiderosis, that is to say a local or general increase in iron levels in otherwise undamaged body tissue, is involved. This also includes pathological conditions that develop in patients after repeated blood transfusions or repeated dialysis treatment where the kidney function is impaired or has failed completely. Owing to its complex-forming properties, desferrioxamine B has also proved to be active in the case of diseases caused by iron(III)-dependent microorganisms and parasites, such as, especially, malaria. Also, its formation of complexes with other trivalent metals can be used for the excretion of those metals from the organism, for example for the removal of aluminium in the case of dialysis encephalopathy and osteomalacia, and in the case of Alzheimer's disease.

However, the fact that desferrioxamine B and its salts are on the one hand insufficiently active when administered orally, and are on the other hand rapidly excreted when administered parenterally, has proved to be a disadvantage. For this reason the active substance is usually administered by means of a slow subcutaneous infusion, which either requires hospitalisation of the patient or, in the case of outpatient treatment, the use of a portable mechanical device, such as an infusion syringe operated by an electrical drive. Apart from their inconvenience, such methods of treatment are relatively costly and, as a result, their use is severely restricted; in particular, under such circumstances large-scale treatment in third world countries is in practice excluded. The consequence of the short residence time of desferrioxamine B in the organism is that in the case of conventional forms of administration a large proportion of the active ingredient is excreted again, unused, before it has the desired effect.

the novel compounds of formula I with the longer polyethylene glycol chains in the N-acyl radical exhibit an unexpectedly slow rate of excretion and thus a prolonged residence time in the organism. Consequently it is possible for these desferrioxamine B derivatives to be used in the form of bolus injections at intervals customary for parenteral administration, for example from 1 to 3 times daily. An especially important advantage is that the compounds of the invention have surprisingly good solubility both in organic solvents (such as halogenated lower alkanes, for example chloroform and dichloromethane), and, especially, in water (up to approximately 30% by weight). The extraordinarily good solubility in water is especially important for parenteral forms of medicaments, all the more so since the neutral compounds of formula I can be used in free form and the use of acid addition salts, such as are employed in the case of desferrioxamine B, can be avoided. By suitable selection of the polyethylene glycol sequence it is possible, in addition, for the desired physical and physiological properties to be more finely adjusted and optimised for specific purposes.

The novel compounds of formula I in which $A_1$, $A_2$ and/or $A_3$ are acyl radicals have proved substantially more effective than desferrioxamine B and its salts when administered orally, and can be used accordingly.

The compounds of formula I according to the invention can therefore be used in the same indications for which desferrioxamine B or its salts, such as the methanesulfonate, can be used, that is to say for the treatment of the above-mentioned pathological conditions.

Owing to their high solubility and good tolerability, the complexes of compounds of formula I in which $A_1$, $A_2$ and $A_3$ are hydrogen, especially with suitable paramagnetic and/or radioactive metals, can be used as contrast agents in diagnostic medicine, for example X-ray, radionuclide, ultrasound and/or nuclear magnetic resonance diagnostics.

In so far as polyethylene glycol monoalkyl ethers, which are used in the manufacture of compounds of formula I and in the preparation of starting materials and intermediates for the manufacture thereof, contain a certain number, for example more than 3 to 4 units of the formula $-(CH_2-CH_2-O)-$ (Ia), they are almost impossible to obtain in the form of homogeneous compounds but normally exist as mixtures of several polyethylene glycol monoalkyl ethers, and therefore result in compounds of formula I that are normally in the form of corresponding mixtures in which the individual compounds differ in the number of units of formula Ia they contain, and accordingly in the present case the number of these units is indicated as an average. That is to say, in a compound of formula I having an average value for n of at least 9, the individual compounds of formula I may have from approximately 5 to approximately 13 units of formula Ia. Preferably, the compounds exhibit average values for n of from approximately 9 to approximately 115, especially of approximately from 10 to 17. That is to say, the average molecular weight of the repeating units of formula Ia is at least approximately 396, preferably from approximately 440 to approximately 5060, and especially from approximately 440 to approximately 748.

An alkyl radical R is especially methyl, but can also be ethyl, n-propyl, isopropyl, n-butyl or tert.-butyl, whilst m is especially 0.

The radicals $A_1$, $A_2$ and $A_3$ may be different from one another but preferably have the same meaning. Acyl radicals $a_1$, $A_2$ and $A_3$ are, for example, the corresponding radicals of carboxylic acids or of carbonic acid monoesters or monoamides.

An acyl radical $A_1$, $A_2$ and/or $A_3$ corresponds, for example, to the formula $Z-C(=O)-$ (Ib), in which Z is hydrogen, a hydrocarbyl radical $R^o$ that, together with the carbonyl group, forms the acyl radical of an unsubstituted or substituted acyclic, carbocyclic, carbocyclic-acyclic, heterocyclic or heterocyclic-acyclic carboxylic acid, or a hydrocarbyloxy radical of the formula $R^o-O-$ that, together with the carbonyl group, forms the acyl radical of a monoesterified carbonic acid, or Z is a hydrocarbylamino radical of the formula $R^o-N(R^1)-$ in which $R^1$ is hydrogen or has the meaning of $R^o$, especially the meaning given hereinafter, and, together with the carbonyl group, forms the acyl radical of a mono- or di-substituted carbamic acid.

The hydrocarbyl radical $R^o$ is an acyclic, carbocyclic or carbocyclicacyclic hydrocarbon radical that preferably has a maximum of 40, and especially a maximum of 20, carbon atoms and may be saturated or unsaturated, unsubstituted or substituted. Instead of one, two or more carbon atoms it may alternatively contain identical or different hetero atoms in the acyclic and/or cyclic moiety, such as, especially, oxygen, sulfur and nitrogen; in the latter case it may be designated as a heterocyclic or heterocyclic-acyclic radical.

Unsaturated radicals are those that contain one or more double and/or triple bonds. Cyclic radicals in which at least one 6-membered carbocyclic or 5- to 8-membered heterocyclic ring contains the maximum number of non-cumulated double bonds are designated as aromatic. Carbocyclic radicals in which at least one ring is in the form of a 6-membered aromatic ring are designated as aryl radicals.

Unless indicated otherwise, organic radicals designated "lower" contain up to and including 7, preferably up to and including 4, carbon atoms.

An acyclic hydrocarbon radical is especially alkyl, alkenyl, alkadienyl or alkynyl, which is branched or, preferably, linear, such as lower alkyl, for example methyl, ethyl, n-propyl, isopropyl, n-butyl or tert.-butyl, or also n-pentyl, n-hexyl or n-heptyl, or higher alkyl, for example n-octyl, n-dodecyl or n-hexadecyl, lower alkenyl, for example allyl or methallyl, or lower alkynyl, for example propargyl.

A carbocyclic hydrocarbon radical is especially a mono-, bi-or polycyclic cycloalkyl, cycloalkenyl or cycloalkadienyl radical, or a corresponding aryl radical containing aromatic rings, preferably one having a maximum of 12 ring carbon atoms and containing 5-to 7-membered, especially 6-membered, rings. Carbocyclic-acyclic radicals are those in which an acyclic radical, especially one having up to and including 7, preferably up to and including 4, carbon atoms, such as lower alkyl or lower alkenyl, for example methyl, ethyl or vinyl, carries one or more carbocyclic, optionally aromatic radicals.

An aryl radical is especially a phenyl radical, or also a naphthyl radical, such as 1- or 2-naphthyl, a biphenylyl radical, such as, especially, 4-biphenylyl, or also an anthryl, fluorenyl or azulenyl radical, or an analogue thereof with one or more saturated rings. Preferred aryl-lower alkyl and -lower alkenyl radicals are, for example, phenyl-lower alkyl and phenyl-lower alkenyl having a terminal phenyl radical, such as, for example, benzyl, and phenethyl, and styryl and cinnamyl, respectively, and also o-, m- and p-tolyl.

Heterocyclic radicals, including heterocyclic-acyclic radicals, are especially monocyclic, or alternatively bi- or poly-cyclic, aza, thia, oxa, thiaza, oxaza, diaza, triaza or tetraza radicals of aromatic character, as well as corresponding partially or, especially, fully saturated heterocyclic radicals of this kind; such radicals may optionally, for example as in the case of the above-mentioned carbocyclic radicals or aryl radicals, carry other acyclic, carbocyclic or heterocyclic radicals and/or may be mono-, di- or poly-substituted by functional groups. The acyclic moiety in heterocyclic-acyclic radicals has, for example, the meaning given in relation to the corresponding carbocyclic-acyclic radicals. If a heterocyclyl radical as a direct substituent $R^o$ is positioned at the oxygen or nitrogen in the radical Z, its free valency originates from one of its carbon atoms.

As has already been mentioned, a hydrocarbyl radical (including a heterocyclyl radical) $R^o$ may be substituted by one, two or more identical or different substituents, the following substituents being especially suitable: free, etherified and esterified hydroxy groups; mercapto and lower alkylthio groups and unsubstituted or substituted phenylthio groups; halogen atoms, such as chlorine and fluorine, but also bromine and iodine; oxo groups that may be in the form of formyl and keto groups, and also in the form of corresponding acetals and ketals; and nitro groups; primary, secondary and, preferably, tertiary amino groups, primary or secondary amino groups protected by conventional protecting groups, acylamino groups and diacylamino groups, and also optionally functionally modified sulfo groups, such as sulfamoyl groups, or sulfo groups in salt form. These groups do not substitute the carbon atom from which the free valency to the oxygen originates; preferably, they are separated from that free valency, and thus from the hetero atom, by at least two carbon atoms. The hydrocarbyl radical may also contain free and functionally modified carboxy groups, such as carboxy groups present in salt form or esterified carboxy groups; carbamoyl, ureidocarbonyl or guanidinocarbonyl groups that may or may not contain one or more substituents; and cyano groups.

An etherified hydroxy group present as a substituent in the hydrocarbyl radical is, for example, a lower alkoxy group, such as a methoxy, ethoxy or tert.-butoxy group, which may also be substituted, for example, by halogen atoms, especially in the 2-position, or by lower alkoxy, especially in the 2-position, such as in the 2-methoxyethoxy radical. An especially preferred form of etherified hydroxy group is an oxaalkyl radical in which a preferably linear alkyl contains, instead of several carbon atoms, oxygen atoms that are separated from one another by several, especially 2, carbon atoms, so that they form an optionally repeated group of the formula $-(-CH_2-CH_2-O)_x-$ (Ic) in which x has an average value of from 1 to 17, for example from 1 to approximately 8, preferably from 1 to 4.

An esterified hydroxy group present as a substituent in the hydrocarbyl radical may contain an acyl radical having up to and including 12 carbon atoms that, within this total number of carbon atoms, may be substituted analogously to the radical of formula Ib, but may also be lactonised by a carboxy group also present in the hydrocarbyl radical.

An esterified carboxy group present as a substituent in the hydrocarbyl radical is one that is esterified by one of the above-described hydrocarbon radicals, preferably a lower alkyl or phenyl-lower alkyl radical; examples of esterified carboxy groups are especially methoxy-, ethoxy-, tert.-butoxy- and benzyloxy-carbonyl groups, and also a lactonised carboxy group.

A preferred amino group is, for example, one of the formula

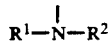

in which $R^1$ and $R^2$, independently of one another, are each hydrogen, unsubstituted acyclic $C_1-C_7$ hydrocarbyl, such as, especially, $C_1-C_4$ alkyl or $C_1-C_4$ alkenyl, or monocyclic unsubstituted or $C_1-C_4$ alkyl-, $C_1-C_4$ alkoxy-, halo- and/or nitro-substituted aryl, aralkyl or aralkenyl having a maximum of 10 carbon atoms, it being possible for two carbon-containing radicals $R^1$ and $R^2$ to be bonded to one another by a carbon-carbon bond or by an oxygen or sulfur atom or by a nitrogen atom that is unsubstituted or substituted by hydrocarbyl, for example lower alkyl. In such a case the radicals form, together with the nitrogen atom to which they are bonded, a nitrogen-containing heterocyclic ring.

In a preferred acyl radical of formula Ib a hydrocarbyl radical $R^o$, for example, $C_1-C_{19}$ alkyl or $C_2-C_{19}$ alkenyl, is especially one that has a linear chain when there are more than 5 carbon atoms and that may carry, for example, the following substituents: carboxy, which may optionally be present in salt form or in functionally modified form, for example as cyano, a carbamoyl group or $C_1-C_4$-alkoxycarbonyl, and which is preferably in the ω-position, an amino group of the above-defined formula

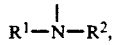

or one or more halogen atoms, especially fluorine or chlorine, which are preferably in α-position to the carbonyl group. Another preferred acyl radical of formula Ib is bicyclic or especially monocyclic aroyl, especially benzoyl, which may contain one or more substituents, such as halogen, especially chlorine or fluorine, nitro, $C_1-C_4$ alkyl, especially methyl, hydroxy and etherified hydroxy, especially $C_1-C_4$ alkoxy, such as methoxy, phenoxy and methylendioxy, and also carboxy, which may also be in salt form or in the form of cyano or of $C_1-C_4$ alkoxycarbonyl. Preferably, aroyl radicals have no more than 2, but especially have only one, such substituent. Also preferred are analogous heteroaroyl radicals, especially those that contain pyridyl, furyl, thienyl or imidazolyl, or analogues thereof with a fused-on benzo ring, such as quinolinyl, isoquinolinyl, benzofuryl or benzimidazolyl, it also being possible for these to be unsubstituted or substituted, for example in the manner indicated above. Preferred acyl radicals of this kind are, for example, also phenylacetyl or cinnamoyl, which may be substituted, for example, in the manner indicated above.

Carboxylic acids forming the basis of the especially preferred acyl radical of formula Ib are, for example, aliphatic monocarboxylic acids having a maximum of 20 carbon atoms, such as lower alkanecarboxylic acids, for example acetic, propionic, butyric, isobutyric, valeric, isovaleric, caproic, trimethylacetic, oenanthic and diethylacetic acid and also lauric, myristic, palmitic and stearic acid as well as oleic acid, elaidic acid, linoleic acid and linolenic acid, but also corresponding halogenated lower alkanecarboxylic acids, such as trifluoroacetic acid, chloroacetic acid, bromoacetic acid and α-bromoisovaleric acid, carbocyclic and carbocyclic-acyclic monocarboxylic acids, for example cyclopropane-, cyclopentane- or cyclohexane-carboxylic acid, and cyclopentane- or cyclohexane-acetic acid or -propionic acid, respectively; aromatic carbocyclic carboxylic acids, for example benzoic acid, that may be mono- or poly-substituted, for example in the manner indicated above; aryl- or aryloxy-lower alkanecarboxylic acids and the analogues thereof unsaturated in the chain, such as phenylacetic, phenoxyacetic, phenylpropionic and cinnamic acids each unsubstituted or substituted, for example in the manner indicated above for benzoic acid; and heterocyclic acids, for example furan-2-carboxylic acid, 5-tert.-butylfuran-2-carboxylic acid, thiophene-2-carboxylic acid, nicotinic or isonicotinic acid, 4-pyridinepropionic acid, and pyrrole-2- or -3-carboxylic acids unsubstituted or substituted by lower alkyl radicals; also corresponding α-amino acids, especially the naturally occurring α-amino acids of the L-series, for example glycine, phenylglycine, proline, leucine, valine, tyrosine, histidine and asparagine, in unprotected form or in N-protected form, in which the amino group is substituted by a conventional amino-protecting group; and also dicarboxylic acids, such as oxalic acid, malonic acid, mono- or di-lower alkylmalonic acids, succinic acid, glutaric acid, adipic acid, maleic acid, fumaric acid or erucic acid, a phthalic, quinolinic, isoquinolinic or phenylsuccinic acid unsubstituted or substituted by halogen, such as fluorine, chlorine or bromine, lower alkyl, hydroxy, lower alkoxy and/or by nitro, as well as, also, glutamic acid and aspartic acid, the last two acids preferably having protected amino groups. The second carboxy group in dicarboxylic acids does not need to be in free form, but may be functionally modified, for example in the form of a $C_1$-$C_4$alkyl ester, an amide or a salt, preferably a physiologically tolerable salt, with a salt-forming basic component. There are suitable especially metal or ammonium salts, such as alkali metal and alkaline earth metal salts, for example sodium, potassium, magnesium or calcium salts, and ammonium salts with ammonia or suitable organic amines.

An acyl radical derived from a monoester of carbonic acid may be represented, for example, by the formula $R^o$—O—C(=O)— (Id). Acyl radicals of this kind are, for example, those in which $R^o$ is an acyclic hydrocarbyl radical, such as $C_1$-$C_{20}$alkyl, $C_2$-$C_{20}$hydroxyalkyl in which the hydroxy group is in any position except the 1-position, but is preferably in the 2-position, cyano-[$C_1$-$C_{20}$]-alkyl in which the cyano group is preferably in the 1- or ω-position, or carboxy-[$C_1$-$C_{20}$]-alkyl in which the carboxy group is preferably in the 1- or ω-position and may optionally be in salt form or in the form of a carbamoyl group or of $C_1$-$C_4$alkoxycarbonyl or benzyloxycarbonyl, and also a linear (mono-, di- to hexa)-oxaalkyl radical having from 4 to 20 chain members wherein one or more of the carbon atoms, from C-3 on, of a linear $C_4$-$C_{20}$alkyl have been replaced by oxygen atoms that are separated from one another by at least 2 carbon atoms and are preferably in positions 3, 6, 9, 12, 15 and 18.

An acyl radical derived from a carbamic acid may be represented, for example, by the formula $R^o$—N($R^1$)—C(=O)— (Ie). Examples of such acyl radicals are especially those in which $R^1$ is hydrogen and $R^o$ is unsubstituted $C_1$-$C_{20}$alkyl or -alkenyl, and a preferred group of carbamic acid acyl radicals is that of the formula $R_a^1$O—CO—Alk—NH—C(=O)— (If) in which $R_a^1$ is $C_1$-$C_4$alkyl and Alk is $C_1$-$C_7$alkylene that is unsubstituted or substituted by hydroxy, $C_{1-4}$alkanoyloxy, amino, carboxy, $C_{1-4}$alkoxycarbonyl, carbamoyl, phenyl, hydroxyphenyl, methoxyphenyl or indolyl. This alkylene radical may be branched or unbranched, it being possible for the two free valencies to originate from the same or from two different carbon atoms; the radical may also carry one of the above-mentioned substituents at any carbon atom. Preferred are linear alkylene radicals with the free valencies at the terminal carbon atoms, such as tri- to hepta-methylene and ethylene, which may contain substituents, such as, especially, carbamoyl or $C_{1-4}$alkoxycarbonyl, especially methoxy- or ethoxy-carbonyl, or primary amino, preferably at their terminal carbon atoms; the first two kinds of substituent are bonded preferably to that end of the alkylene radical which is bonded to the amino group, and the latter is preferably at that end which is bonded to the carbonyl group. Also preferred are linear alkylene radicals or alkylene radicals branched not more than once, the two free valencies of which originate from the same, and preferably from a terminal, carbon atom, that is to say 1,1-alkylidene radicals, for example especially methylene, and also ethylidene or 1,1-propylidene. These may contain, for example, one of the above-mentioned substituents, preferably at the terminal carbon atom, for example free amino, such as in 4-amino-1,1-butylidene or 5-amino-1,1-pentylidene, carbamoyl or $C_{1-4}$alkoxycarbonyl, such as, for example, in 2-carbamoyl-1,1-ethylidene, 2-(methoxy- or ethoxy)-carbonyl-1,1-ethylidene or corresponding 3-substituted 1,1-propylidene, also hydroxy or $C_{1-4}$alkanoyloxy, for example acetoxy, which is preferably in the 2-position, such as in 2-hydroxy-1,1-ethylidene or 2-hydroxy-1,1-propylidene, and corresponding O-acylated, especially O-acetylated, radicals. Cyclic substituents are situated preferably at the methylene group or alternatively in the 2-position of an ethylidene radical.

An especially preferred alkylene radical is a corresponding radical that together with the amino and carbonyl groups forms a radical of the partial formula —NH—Alk—C(=O)— (Ig), which corresponds to the structure of natural α-amino acids, in the form of their individual optical isomers or racemic mixtures. Corresponding acyl radicals are those of the formula If in which $R_a^1$ has the meanings given above and the partial formula Ig corresponds to the radical of a natural α-amino acid in the form of an optical isomer or a racemate. The naturally occurring isomer of the L-series is preferred as the optically individual form, and the racemates are preferred as the isomeric mixtures. The radical of the partial formula Ig is especially the glycine radical (-Gly-), and in the formula If $R_a^1$ is especially methyl or ethyl.

Salts of compounds of the above formula I having salt-forming properties are derived from those that contain a salt-forming group, for example an amino group or a carboxy group, as substituent in an acyl radical $A_1$, $A_2$ and/or $A_3$. Basic compounds of the formula I can form acid addition salts, especially pharmaceutically acceptable, non-toxic acid addition salts, with inorganic acids, for example hydrochloric acid, hydrobromic acid, sulfuric acid or phosphoric acids, or with organic acids, such as sulfonic acids, for example benzenesulfonic acid, p-toluenesulfonic acid, naphthalene-2-sulfonic acid, methanesulfonic acid, ethanesulfonic acid, 2-hydroxyethanesulfonic acid and ethane-1,2-disulfonic acid, and also carboxylic acids, for example acetic acid, propionic acid, glycolic acid, succinic acid, maleic acid, hydroxymaleic acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and acidic compounds of the formula I can form salts of the kind described above.

Metal complexes of compounds of the formula I in which $A_1$, $A_2$ and $A_3$ are hydrogen are especially those with suitable paramagnetic transition metals, including lanthanides, and with metals of main group 3 of the Periodic Table, optionally in the form of radionuclides, especially with corresponding trivalent metals. Examples are especially trivalent iron, manganese and chromium, and examples of corresponding lanthanides are especially gadolinium, also dysprosium, trivalent europium, holmium, lanthanum and trivalent ytterbium. Suitable metals of main group 3 of the Periodic Table are preferably gallium and indium, especially the radioactive isotopes, for example $^{67}$Ga and $^{115}$In; additional nuclides are, for example, the radioactive isotopes of the above-mentioned metals, for example trivalent $^{140}$La or $^{169}$Yb.

The compounds of the present invention have valuable properties; those of the formula I have physiological activities analogous to those of desferrioxamine B and can therefore be used for the same purpose, and the described metal complexes of compounds of the formula I in which $A_1$, $A_2$ and $A_3$ are hydrogen have properties making them suitable for use as contrast agents, and can therefore be used as such in diagnostics.

Compared with desferrioxamine B, the advantage of compounds of the formula I, the action of which can be demonstrated, for example, in the so-called biliary rat by way of the increased excretion of iron in bile and in urine, resides in their substantially better solubility, a property which renders them available for standard parenteral administration. Further advantages are that the compounds are neutral, are well tolerated locally, and have a longer residence time in the organism. Furthermore, the compounds of formula I in which $A_1$, $A_2$ and/or $A_3$ are an acyl radical exhibit the desired activity when administered orally. The novel compounds of formula I can therefore be used for the same indications as desferrioxamine B, for example for the treatment of functional disorders in which the concentration of trivalent iron in body cells is abnormally high, such as for the treatment of haemochromatosis and haemosiderosis, and since, moreover, they also bind aluminium ions, for example for the treatment of dialysis encephalopathy, osteomalacia and Alzheimer's disease. The above-mentioned metal complexes, which are excellently soluble in water and in addition are well tolerated, can be used as contrast agents (so-called image enhancers) in diagnostic medicine, for example in X-ray, radionuclide and ultrasound diagnostics and/or, especially, in magnetic resonance diagnostics (MRI: magnetic resonance imaging).

The invention relates especially to compounds of the formula I in which R, X and m have the meanings given above, n has an average value of from approximately 9 to approximately 115 and each of the radicals $A_1$, $A_2$ and $A_3$, independently of the others, is hydrogen or a radical of the formula Z—C(=O)— (Ib) in which Z is hydrogen or a hydrocarbyl radical $R^0$ that, together with the carbonyl group, forms the acyl radical of an unsubstituted or substituted acyclic, carbocyclic, carbocyclic-acyclic, heterocyclic or heterocyclic-acyclic carboxylic acid, or a hydrocarbyloxy radical of the formula $R^0$—O— that, together with the carbonyl group, forms the acyl radical of a monoesterified carbonic acid, or a hydrocarbylamino radical of the formula $R^0$—N($R^1$)— in which $R^1$ is hydrogen or has the meaning of $R^0$ and which, together with the carbonyl group, forms the acyl radical of a mono- or di-substituted carbamic acid, and to salts of such compounds having salt-forming properties, and to complexes of such compounds, in which $A_1$, $A_2$ and $A_3$ are hydrogen, with trivalent paramagnetic transition metals, including corresponding lanthanides, metals of main group 3 of the Periodic Table and radionuclides.

The invention relates especially to compounds of the formula I in which R, X and m have the meanings given above, n has an average value of from approximately 10 to approximately 17, and each of the radicals $A_1$, $A_2$ and $A_3$, independently of the others, is hydrogen, alk(en)oyl having up to and including 20 carbon atoms, alkoxycarbonyl having up to and including 20 carbon atoms in the alkyl moiety, wherein up to and including 5 methylene groups may be replaced by oxygen atoms and in each case two carbon atoms separate the oxygen atoms from one another, or alkylaminocarbonyl having up to and including 20, preferably up to and including 7, carbon atoms in the alkyl moiety, which may be unsubstituted or substituted by carboxy, lower alkoxycarbonyl having up to and including 4 carbon atoms in the lower alkyl moiety, carbamoyl and/or by amino, hydroxy, mercapto, lower alkylthio having up to and including 4 carbon atoms, phenyl or by hydroxyphenyl, and to salts of such compounds having salt-forming properties, or complexes of such compounds, in which $A_1$, $A_2$ and $A_3$ are hydrogen, with trivalent paramagnetic transition metals, including corresponding lanthanides, and with suitable metals of main group 3 of the Periodic Table, and with suitable radionuclides.

The invention relates especially to compounds of the formula I in which R has the meaning given above and is especially methyl, X has the meaning given above and m is 0, n has an average value of from approximately 10 to approximately 17, especially from approximately 11 to approximately 12, and each of the radicals $A_1$, $A_2$ and $A_3$, independently of the others, is especially hydrogen, or also alkanoyl having up to and including 12, preferably from 6 up to and including 12, carbon atoms, for example octanoyl, alkoxycarbonyl in which alkyl has up to and including 7, preferably up to and including 4, carbon atoms, wherein one or two methylene groups may be replaced by oxygen and oxygen atoms are in each case separated from each other by two carbon atoms, alkyl being, for example, methyl or ethyl, or may be alkylaminocarbonyl in which alkyl has up to and including 7, preferably up to and including 4, carbon atoms, and which may carry as substituent in the 2-position, especially in the 1-position, alkoxycarbonyl in which alkyl contains up to and including 4 carbon atoms and is, for example, methyl or ethyl, especially alkoxycarbonylmethylaminocarbonyl in which alkyl has up to and including 4 carbon atoms and is, for example, methyl or ethyl, and to complexes of such compounds, in which $A_1$, $A_2$ and $A_3$ are hydrogen, with trivalent paramagnetic transition metals, including corresponding lanthanides, and with metals of main group 3 of the Periodic Table, and with suitable radionuclides.

The invention relates especially to compounds of the formula I in which R is methyl, X has the meaning given above and m is 0, n has an average value of from approximately 10 to approximately 17, especially from approximately 11 to approximately 12, and each of the radicals $A_1$, $A_2$ and $A_3$ is hydrogen, and to complexes of such compounds with trivalent paramagnetic transition metals, including lanthanides, especially with iron(III) and manganese(III), and also gadolinium(III), or with metals of main group 3 of the Periodic Table, especially with gallium(III) and indium(III), and with suitable radionuclides.

The invention relates especially to the compounds described in the Examples.

The compounds of formula I can be manufactured in a manner known per se, inter alia by analogy processes generally known from peptide chemistry, for example by reacting a compound of the formula $$R-O-(CH_2-CH_2-O)_n-Y_1 \quad (III)$$

with a compound of the formula

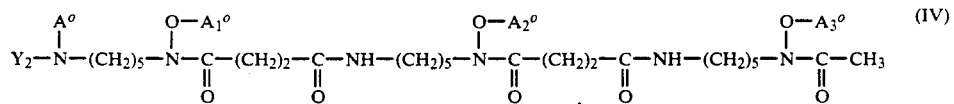

or with a salt thereof, in which (a) $Y_2$ is hydrogen and $Y_1$ is a group of the formula $-X-Z_1$ (IIIa) in which $Z_1$ is a group Z that can be removed together with the hydrogen $Y_2$ to form the bond between the reactants, or (b) $Y_1$ is hydrogen and $Y_2$ is a group of the formula $Z_2-X-$ (IVa) in which $Z_2$ is a group Z or, if m in a radical X is 0, together with $A^o$ forms a bond, and in which $A^o$ is hydrogen or, if $Y_2$ is hydrogen, is an amino-protecting group, and each of the radicals $A_1^o$, $A_2^o$ and $A_3^o$, independently of the others, is hydrogen, a suitable protecting group or an acyl radical, functional groups in acyl radicals $A_1^o$, $A_2^o$ and $A_3^o$ optionally being in protected form and, if desired or necessary, protecting groups present in a compound obtainable in accordance with the invention are removed and, if desired, in a compound of the formula I obtainable in accordance with the invention in which at least one of the groups $A_1$, $A_2$ and $A_3$ is hydrogen, this is replaced by an acyl radical and/or, if desired, a compound of the formula I obtainable in accordance with the invention in which $A_1$, $A_2$ and $A_3$ are hydrogen is converted into a metal complex and/or, if desired, a salt obtainable in accordance with the invention of a salt-forming compound of the formula I is converted into the free compound or a compound obtainable in accordance with the invention having salt-forming properties is converted into a salt.

A group Z that can be removed together with hydrogen to form the desired bond is, for example, reactive esterified hydroxy, especially hydroxy esterified by a strong, preferably inorganic, acid, such as halogen (ester with hydrohalic acid) having an atomic number of at least 19, especially chlorine, or also bromine or iodine, or azido (ester with hydrazoic acid). Other removable groups Z are suitable groups that are bonded by way of a ring nitrogen atom, preferably monocyclic, especially pentacyclic, or azacyclic groups, for example diazacyclic groups, such as 1-imidazolyl. The latter groups are customarily used in starting materials of the formulae III and IV in which m in the radical X of the partial formulae IIIa and IVa, respectively, is 0.

Protecting groups $A_1^o$, $A_2^o$ and/or $A_3^o$ are especially suitable organic silyl groups, such as, for example, groups of the formula $(R_a)(R_b)(R_c)Si-$ (IVb) in which $R_a$ and $R_b$, independently of one another, are each a hydrocarbon radical, for example lower alkyl, such as ethyl, tert.-butyl, n-pentyl, isopentyl or n-hexyl, especially methyl, or unsubstituted or lower alkyl-substituted phenyl or phenyl-lower alkyl, for example phenyl, p-tolyl, benzyl or phenylethyl, but are preferably identical substituents, and $R_c$ is halogen, especially chlorine, or is one of the hydrocarbon radicals mentioned for $R_a$ and $R_b$, especially methyl. Suitable silyl groups are, for example, tribenzylsilyl, phenyl-dimethylsilyl, benzyl-dimethylsilyl, hexyl-dimethylsilyl, tert.-butyl-dimethylsilyl, triethylsilyl, diethyl-chlorosilyl, especially dimethyl-chlorosilyl and, more especially, trimethylsilyl.

An amino-protecting group $A^o$ that does not affect the reactivity of the amino group is preferably also an organic silyl group, such as one of those mentioned above, especially dimethylchlorosilyl and, more especially, trimethylsilyl. Such a group has, moreover, an activating action on the reactivity of the amino group and can therefore also act as an amino-activating group.

The reaction is carried out in a manner known per se. Variant (a), according to which a starting material of the formula III, in which $Y_1$ is a radical of the formula IIIa wherein $Z_1$ is a reactive esterified hydroxy group, especially halogen and, more especially, chlorine, is reacted with a starting material of the formula IV, in which $Y_2$ is hydrogen and $A_1^o$, $A_2^o$ and $A_3^o$ are other than hydrogen, suitable protecting groups usually being organic silyl groups, especially dimethylchlorosilyl and, more especially, trimethylsilyl, and functional groups in acyl radicals that might enter into reaction with a compound of formula III preferably being in protected form, and Ao is preferably an amino-protecting group, usually an organic silyl group, especially dimethylchlorosilyl and, more especially, trimethylsilyl, is preferably carried out under basic conditions in the presence of a suitable acid-binding aprotic base. Such bases are, for example, corresponding organic bases, for example tertiary amines, such as tri-lower alkylamines, for example triethylamine, ethyldiisopropylamine or tributylamine, di-lower alkylaniline, for example N,N-dimethylaniline or N,N-diethylaniline, N-lower alkyl (oxa- or aza-)-lower alkyleneamines, for example N-methylpiperidine, N-ethylpiperidine, N-methylmorpholine, N-ethylmorpholine or 1,4-dimethylpiperazine, or nitrogen-containing heteroaromatic bases, for example pyridine, collidine or quinoline. The reaction is preferably carried out with the exclusion of water, customarily in the presence of a suitable aprotic solvent or solvent mixture, if necessary while cooling or heating and/or under an inert gas atmosphere.

If a starting material of the formula III is used in which $Y_1$ is a radical of the formula IIIa wherein m in the partial formula for X is O and $Z_1$ is an azacyclic group bonded by way of a ring nitrogen atom, such as 1-imidazolyl, the reaction can be carried out with a compound of the formula IV in which $A_1^o$, $A_2^o$ and/or $A_3^o$, apart from an acyl radical or a protecting group, may also be hydrogen, and in which Ao, apart from an amino-protecting group, may also be hydrogen. The reaction is carried out in the presence of a solvent or solvent mixture, it also being possible to use protic solvents, including water, and also, if necessary, while cooling or heating and/or under an inert gas atmosphere.

Correspondingly, the reaction of a starting material of the formula III in which $Y_1$ is hydrogen is carried out with a starting material of the formula IV in which $Y_2$ is a radical of the formula IVa, wherein $Z_2$ is preferably an esterified hydroxy group, especially halogen, for example chlorine. As mentioned, if m in the partial formula for X is O, $Z_2$ together with Ao can form a bond, in which case, in the starting material of the formula IV participating in the reaction, the group $Z_2$ in the radical of the formula IVa forms, together with the nitrogen atom containing the radical $Y_2$, an isocyanato group. The reaction conditions for variant (a) of the general process are also applied analogously to variant (b) thereof.

The protected functional groups present in the compounds obtainable in accordance with the process can be freed in a manner known per se. In particular, the groups protected by organic silyl groups, such as, for example, the hydroxy groups in the desferrioxamine moiety of compounds of the formula I, and also the amino group containing a silyl group, can be freed by solvolysis in the course of working up, for example by treating the reaction product with a protic reagent, such as a lower alkanol, for example methanol or ethanol, and/or water, it being possible for the solvolysis, if appropriate, also to be acid-catalysed by the addition of a suitable acid, for example hydrogen chloride.

Usually, the starting materials of the formulae III and IV, in which $Y_1$ and $Y_2$ are other than hydrogen, and the starting materials of the formula IV in which $A_1^0$, $A_2^0$ and $A_3^0$ are silyl protecting groups and/or $A^0$ is a silyl group, are manufactured in situ or directly before the actual reaction and without additional working up.

For example, a compound of the formula III in which $Y_1$ is hydrogen may be reacted, preferably in a suitable diluent or mixture of diluents, with a suitable carbonic acid derivative, such as a carbonic acid dihalide, for example phosgene, or with a suitable carbonic acid diamide, the amide moiety being an azacyclic radical bonded by way of a ring nitrogen atom, for example 1,1'-carbonyl-bis-1H-imidazole. In this manner a starting material of the formula III is obtained in which $Y_1$ is a radical of the formula IIIa, m in the partial formula for X is 0 and $Z_1$ has the meaning given above; such a starting material is usually reacted with the reactant of formula IV without separate working up and purification. A starting material of the formula III in which $Y_1$ is a radical of the formula IIIa, wherein m in the partial formula for X is 1 and $Z_1$ is, for example, halogen, especially chlorine, can be manufactured in situ by reacting a compound of the formula III in which $Y_1$ is hydrogen with a halo-, for example chloro-sulfonylisocyanate. If the so-obtainable compound is used as a starting material, compounds of the formula I can be obtained in which m in the partial formula for X is 1 and the group of the partial formula —X—NH is the bivalent radical of the formula —C(=O)—NH—S(O)$_2$—NH—.

The starting materials of the formula IV in which $Z_2$ in the partial formula IVa is other than hydrogen can be manufactured in an analogous manner; in this process usually desferrioxamine B or derivatives thereof are used in which functional groups that might participate in the reaction are in protected form. Starting from a suitable intermediate, it is possible, for example, to obtain compounds of the formula IV in which m in the partial formula for X is 1 and the group of the partial formula —X—NH— is the bivalent radical of the formula —S(O)$_2$—NH—C(=O)—NH— by reacting the intermediate with a reactive amino group, for example with a halosulfonylisocyanate, such as chlorosulfonylisocyanate.

In a starting material of the formula IV in which at least one of the radicals $A_1$, $A_2$ and $A_3$ is hydrogen, hydroxy groups present are preferably protected by organic silyl groups of the formula IVb, it also being possible simultaneously for the amino group in such a starting material in which $Y_2$ and $A^0$ are hydrogen to be silylated and activated thereby. In this case such a compound of the formula IV, or an acid addition salt thereof, is reacted in the presence of an aprotic organic base, such as one of those mentioned above, especially pyridine, with a suitable silylating reagent, especially a silyl halide of the formula $(R_a)(R_b)(R_c)$Si-Hal (V), in which $R_a$, $R_b$ and $R_c$ have the meanings given above and Hal is bromine or, especially, chlorine. Especially preferred silylating reagents are, for example, tri-lower alkylsilyl chlorides, such as trimethylsilyl chloride, or also a di-lower alkyldichlorosilane, such as dimethyldichlorosilane. The silylating agent is customarily added in excess; its presence does not adversely affect the main reaction, that is to say the reaction with the component of formula III; on the contrary, it is possible, for example, for traces of moisture, which interfere, to be removed thereby. Consequently, the main reaction can follow the silylation in the same reaction medium and, in addition, be put together with the subsequent solvolytic removal of the silyl groups, so that all 3 steps (manufacture of the starting material of the formula IV, treatment with the component of the formula III and removal of the silyl groups) can be carried out in the same reaction medium.

Suitable protecting groups for the temporary protection of functional groups, such as amino groups, that may be present in acyl radicals $A_1$, $A_2$ and/or $A_3$ in a starting material of the formula IV are the customary protecting groups, such as amino-protecting groups, that are used, for example, in the synthesis of peptides and that, together with corresponding methods for their removal, are described in detail in synoptical reviews and reference works, such as Houben-Weyl, Methoden der organischen Chemie (4th edition), vol 15/I and II, and E. Wüsch (editor), Synthese von Peptiden (Georg-Thieme Verlag, Stuttgart; 1974). It is preferable to use protecting groups that can be removed by acidolysis or under neutral conditions.

Suitable amino-protecting groups apart from the above-mentioned organic silyl groups that are also suitable under certain circumstances are, for example, unsubstituted or substituted trityl, which can be removed, for example, by treatment with 50% acetic acid, 2-nitrophenylsulfenyl, which can be removed, for example, by acid-catalysed solvolysis or acidolysis, for example by treatment with pyridine hydrochloride, unsubstituted or substituted benzyloxycarbonyl, which can be removed, for example, under neutral conditions by hydrogenolysis or acidolysis, tert.-butoxycarbonyl, which can be removed by acidolysis, or allyloxycarbonyl, which can be removed by acidolysis or under mild neutral conditions by treatment with dimedone, or by the reducing action of tributyltin hydride catalysed by palladium-(O)-tetrakis-(triphenylphosphine) complex.

Free carboxy groups contained in a starting material of the formula IV are customarily protected in the form of esterified carboxy groups that can usually be cleaved by means of conventional hydrolysis, especially under the action of bases, such as alkali metal hydroxides, carbonates or hydrocarbonates, or in the form of suitable esters, which can also be cleaved by other methods: for example esters with tertiary alcohols, for example tert.-butanol, can be cleaved by acidolysis, for example by means of hydrogen fluoride or trifluoroacetic acid, or esters with benzylalcohols can be cleaved by means of conventional hydrogenolysis. Carboxy groups can also be protected, for example, in the form of silyl esters that contain as the esterifying grouping, for example, the above-mentioned organic silyl groups, and are cleaved in a manner known per se, that is to say by solvolysis.

Hydroxy groups may be protected, for example, in the form of esters with carboxylic acids, such as with lower alkanoic acids or with monoesters of carbonic acid, for example formates or acetates, or tert-butoxy or benzyloxy carbonates, or in the form of ethers, such as those with tertiary alcohols, for example tert.-butanol, or in the form of acetals, for example in the form of 2-tetrahydropyranyl ether. The first-mentioned type are usually cleaved analogously to the esterified carboxy groups, whilst the two latter types are cleaved, for example, by means of acidolysis.

When the reaction is complete, functional groups present in protected form can be freed in a manner known per se, for example as described.

If desired, in compounds of the formula I obtainable in accordance with the invention in which at least one of the radicals $A_1$, $A_2$ and $A_3$ is hydrogen, this may be replaced by an acyl radical by treating such compounds with agents that introduce an acyl radical. Such agents are, for example, anhydrides of corresponding acids, which include symmetrical, mixed and internal anhydrides. Mixed anhydrides are, for example, those of carboxylic acids with strong inorganic acids, such as hydrohalic acids, for example especially hydrochloric or also hydrobromic or hydriodic acid (that is to say acid halides), or also phosphoric or sulfuric acid, and also hydrazoic acid, or with suitable organic acids, such as carbonic acid lower alkyl semiesters, such as ethyl semiesters, or trifluoroacetic acid. Internal anhydrides are, for example, ketenes (internal anhydrides of carboxylic acids) or isocyanato compounds (internal anhydrides of carbamic acid compounds). Other acylating agents are, for example, suitable activated esters and amides of carboxylic acids, for example corresponding cyanomethyl or pentachlorophenyl esters, and also esters with heterocylic N-hydroxy compounds, for example N-hydroxysuccinimide or N-hydroxybenzotriazole, and also amides of carboxylic acids, for example 1-imidazolides. It is also possible to use as acylating agent a free acid in the presence of a suitable condensing agent, for example dicyclohexylcarbodiimide.

The acylation is carried out in a manner known per se, if necessary while cooling or heating, for example in a temperature range of from approximately $-10°$ to approximately $+100°$ C., and/or under elevated pressure, and/or under an inert gas atmosphere, in heterogeneous phase, such as in suspension, or in homogeneous liquid phase using suitable solvents, and, where appropriate, in the presence of acid-binding agents, such as organic nitrogen-containing bases, for example tertiary amines, such as triethylamine, ethyldiisopropylamine, N,N-dimethylaniline, N-ethylpiperidine or N,N'-dimethylpiperazine, or aromatic heterocyclic bases, for example pyridine, collidine, quinoline or 4-dimethylaminopyridine, or also basic inorganic compounds, such as alkali metal hydroxides, carbonates or hydrocarbonates, as well as salts of carboxylic acids, such as sodium or potassium acetate. It is also possible to use neutral-reacting nitrogen-containing compounds, which may under certain circumstances be used also as solvents, for example carboxylic acid amides, such as dimethylformamide or N-methylpyrrolidone, as well as urethanes or urea.

If necessary, free functional groups present in the acylating reagent are in protected form and can be freed after the acylation reaction; protecting groups are, for example, those mentioned above, and their removal is carried out, for example, by the processes indicated.

The complexes of compounds of the formula I, in which $A_1$, $A_2$ and $A_3$ are hydrogen, with metals are manufactured in a manner known per se by reacting such compounds with a suitable metal compound, such as an inorganic or organic salt or derivative thereof, the starting material and metal reagent usually being used in the form of appropriate solutions. Salts are, for example, inorganic or organic metal salts, such as corresponding metal halides, for example chlorides, inter alia iron(III) chloride or manganese(III) chloride, or sulfates, for example iron(III) sulfate complexed with ammonium sulfate. Derivatives are, inter alia, complexes with certain organic compounds, preferably complexes with suitable $\beta$-dicarbonyl compounds with a binding affinity to the metal ions that is lower than that of compounds of the formula I in which $A_1$, $A_2$ and $A_3$ are hydrogen (that is to say, the negative common logarithm of the dissociation constants (pK) for the complexes of the latter with the metal ions must be greater than for the complexes of the $\beta$-dicarbonyl compounds and the metal ions). Such $\beta$-dicarbonyl compounds are customarily of aliphatic and cycloaliphatic character, it being possible for at least one of the two carbonyl groups, which are in the 1- and 3-positions in relation to one another, to be in enol form, and the two carbonyl groups being available for the complexing of a metal ion and not being sterically hindered. An especially preferred 1,3-dicarbonyl compound is, for example, acetylacetone; acetylacetonates of numerous metals are available commercially.

These derivatives are preferably used in the form of solutions in solvents or solvent mixtures that are not miscible with water at will. For example, the above-mentioned metal acetylacetonates are soluble in a lower alkanecarboxylic acid lower alkyl ester that is not miscible at will, and practically immiscible, with water, such as ethyl acetate, in a suitable, preferably acyclic ether, such as diethyl ether, or in an unsubstituted or halogenated hydrocarbon, for example an aromatic hydrocarbon, such as benzene or toluene, an aliphatic hydrocarbon, such as pentane or heptane, or a halogenated hydrocarbon, such as chloroform or methylene chloride.

Since the complexes obtainable according to the process of compounds of the formula I in which $A_1$, $A_2$ and $A_3$ are hydrogen are not soluble in such solvents but are readily soluble in water, the reaction is customarily carried out by adding a solution or suspension in water of the compound of formula I in which $A_1$, $A_2$ and $A_3$ are hydrogen to a solution of the complex of the $\beta$-dicarbonyl compound and the metal ion in a solvent that is at most partly miscible with water, and stirring the mixture. The reactants can be used in equivalent amounts; it is also possible, however, to use a slight excess, for example 10–20%, of the complex with the $\beta$-dicarbonyl compound. The reaction is preferably carried out at a temperature of from approximately $-20°$ C. to approximately $+150°$ C., especially from approximately $+10°$ C. to approximately $+70°$ C., more especially at room temperature. The reaction temperature to be employed in any individual case depends, inter alia, on the melting or boiling point of the solvent (mixture), on the stability of the reactants and of the complex formed and on the desired reaction rate. If desired or necessary, the reaction can be carried out under pressure and/or under an inert gas atmosphere.

Depending on the procedure, compounds of the formula I according to the invention with salt-forming properties are obtained in free form or in the form of salts. Acid addition salts can be freed from these in a manner known per se, for example by treatment with suitable bases, and salts with bases can be freed also in a manner known per se, for example, by treatment with suitable acids. Acidic compounds of the formula I can be converted into corresponding salts, for example, by treatment with a suitable base, such as an alkali metal or alkaline earth metal hydroxide or carbonate, or with ammonia or an organic base, for example an amine, and basic compounds of the formula I can be converted into corresponding salts, for example, by treatment with a suitable acid, such as an inorganic or organic acid.

Owing to the close relationship between the novel compounds in free form and in the form of their salts, including also those that can be used as intermediates, for example for purification or identification, hereinbefore and hereinafter references to free compounds shall also, where appropriate with regard to context, include the corresponding salts.

The starting materials used in the process according to the present invention are preferably those that result in the compounds described at the beginning as being especially valuable.

The invention relates also to those forms of the process in which a starting material is formed under the reaction conditions or is used in the form of a derivative, for example a salt.

The present invention relates also to compositions, such as pharmaceutical preparations, that contain as active ingredient one of the compounds of the formula I according to the invention. Especially preferred are pharmaceutical preparations and compositions for parenteral, such as especially intravenous, subcutaneous and intramuscular, administration, and also for enteral, such as oral or rectal, administration. The preparations contain the active ingredient on its own or, preferably, together with pharmacologically tolerable adjuncts. The dosage of the active ingredient depends on the disorder to be treated and on the individual and its age, weight and/or condition, and also on the mode of administration, but in general it corresponds in quantity approximately to that used for prolonged infusion with desferrioxamine B or a salt thereof.

The pharmaceutical compositions contain from approximately 5% to approximately 95% of the active ingredient, single dose forms of administration preferably containing from approximately 20% to approximately 90%, and non-single dose forms of administration, such as injection solutions, preferably containing from approximately 5% to approximately 30%, of active ingredient; pharmaceutical preparations in dosage unit form, such as dragées, tablets or capsules and suppositories, contain from approximately 0.1 g to approximately 3.0 g, preferably from approximately 0.3 g to approximately 1.0 g, of the active ingredient.

The pharmaceutical compositions of the present invention are manufactured in a manner known per se, for example by means of conventional mixing, granulating, confectioning, dissolving or lyophilising processes. For example, pharmaceutical compositions for oral use can be obtained by combining the active ingredient with one or more solid carriers, if desired granulating a resulting mixture, and formulating the mixture or granulate, if desired and/or appropriate after the addition of additional adjuncts, into tablets or dragée cores. Injection solutions are prepared preferably by dissolving the active ingredient in deionised pyrogen-free water, where appropriate with the addition of buffers and preservatives, sterile-filtered, and introduced as required into containers and lyophilised.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starches, for example corn, wheat, rice or potato starch, methylcellulose, hydroxypropylmethylcellulose, sodium carboxymethylcellulose and/or polyvinylpyrrolidone and/or, if desired, disintegrators, such as the above-mentioned starches, also carboxymethyl starch, crosslinked polyvinylpyrrolidone, or alginic acid or a salt thereof, such as sodium alginate. Additional adjuncts are especially flow-regulating agents and lubricants, for example silica, talc, stearic acid or salts thereof, such as magnesium or calcium stearate, and/or polyethylene glycol.

Dragée cores are provided with suitable coatings that may be resistant to gastric juices, there being used, inter alia, concentrated sugar solutions that optionally contain gum arabic, talc, polyvinylpyrrolidone, polyethylene glycol and/or titanium dioxide, or lacquer solutions in suitable organic solvents or solvent mixtures or, to produce coatings that are resistant to gastric juices, solutions of suitable cellulose preparations, such as acetylcellulose phthalate or hydroxypropylmethylcellulose phthalate. Colouring substances or pigments may be added to the tablets or dragée coatings, for example for the purposes of identification or to indicate different doses of active ingredient.

Other orally administrable pharmaceutical compositions are dry-fill capsules made of gelatin, and also soft, sealed capsules made of gelatin and a plasticiser, such as glycerine or sorbitol. The dry-filled capsules may contain the active ingredient in the form of a granulate, for example in a mixture with fillers such as corn starch, binders and/or glidants, such as talc or magnesium stearate, and, where appropriate, stabilisers. In soft capsules the active ingredient is preferably dissolved or suspended in suitable liquids, such as fatty oils, paraffin oil or liquid polyethylene glycols, it being possible also for stabilisers to be added.

Other forms of oral administration are, for example, syrups prepared in customary manner that contain the active ingredient, for example, in suspended form and in a concentration of approximately from 5% to 20%, preferably approximately 10%, or in a similar concentration that produces, for example when dispensing 5 or 10 ml, a suitable single dose. Also suitable are, for example, pulverulent or liquid concentrates for preparing shakes, for example in milk. Such concentrates can also be packed in single-dose quantities.

Suitable rectally administrable pharmaceutical preparations are, for example, suppositories that consist of a combination of the active ingredient with a suppository base material. Suitable suppository base materials are, for example, natural or synthetic triglycerides, paraffin hydrocarbons, polyethylene glycols or higher alkanols. It is also possible to use gelatin rectal capsules that contain a combination of the active ingredient with a base material. Suitable base materials are, for example, liquid triglycerides, polyethylene glycols or paraffin hydrocarbons.

There are suitable for parenteral administration especially aqueous solutions of an active ingredient in water-soluble form, and also suspensions of the active ingredient, such as corresponding oily injection suspensions, for which suitable lipothilic solvents or vehicles, such as fatty oils, for example sesame oil, or synthetic fatty acid esters, for example ethyl oleate or triglycerides, are used, or aqueous injection suspensions that contain viscosity-increasing substances, for example sodium carboxymethylcellulose, sorbitol and/or dextran, and, where appropriate, also stabilisers.

The invention relates also to compositions for diagnostic purposes that contain a suitable metal complex of a compound of the formula I in which $A_1$, $A_2$ and $A_3$ are hydrogen, preferably in the form of an aqueous solution or in the form of a dry preparation.

The invention relates also to a method for the treatment of disorders in which, for example, as described above, an excess of iron(III) or aluminium is present in the body, which comprises administering a prophylactically or therapeutically effective amount of a compound of the formula I. For this especially the above-mentioned pharmaceutical compositions are used, a daily dose of from approximately 0.2 g to approximately 10 g, preferably from approximately 0.5 g to approximately 5 g, of a compound according to the invention being administered to a warm-blooded animal weighing approximately 70 kg.

The invention relates also to the use of suitable metal complexes of compounds of the formula I in which $A_1$, $A_2$ and $A_3$ are hydrogen for diagnostic purposes, especially in magnetic resonance diagnostics. Usually aqueous solutions of such metal complexes are employed that are preferably prepared before administration and therefore contain no other additives. The solutions with concentrations of up to approximately 25%, usually of from approximately 10% to approximately 25%, of the metal complex, are customarily used as bolus injections, doses of from approximately 0.01 to approximately 1 mmol/kg, especially from approximately 0.2 to approximately 0.4 mmol/kg of the metal complex being administered parenterally, especially intravenously.

The invention is illustrated by way of the following Examples; temperatures are given in degrees Celsius.

EXAMPLE 1

N-[ω-methoxy-(dodecakis-ethyleneoxy)-carbonyl]-desferrioxamine B, in which dodecakis-ethyleneoxy denotes a radical of the formula $-(CH_2-CH_2-O)_n-$ in which n has an average value of 12.

194.0 ml (1,500 mmol) of trimethylchlorosilane are added at room temperature to a suspension of 86.5 g (132 mmol) of desferrioxamine B-methanesulfonate in 2,000 ml of pyridine; the resulting solution is then stirred at room temperature for 3 hours. The acylating agent, obtained by mixing a solution of 72.6 g (132 mmol) of a polyethyleneglycol monomethyl ether having an average molecular weight of about 560 (Carbowax MPEG 550, Messrs Union Carbide, which contains on average 12 units of the formula $-CH_2-CH_2-O-$) in 1,000 ml of toluene with 66.0 ml (132 mmol) of a 20% solution of phosgene in toluene at 70° C., stirring for 3 hours at that temperature and cooling, is added dropwise to the reaction mixture within a period of 15 minutes at room temperature. The mixture is stirred for 16 hours at room temperature; then, by adding 2,000 ml of methanol excess reagents are destroyed and silyl groups are removed, after which the solvents are distilled off as far as is possible. The residue, still containing a substantial proportion of pyridine, is crystallised from approximately 500 ml of methylene chloride and 1,000 ml of diethyl ether and dried for 16 hours under a high vacuum. The title compound is obtained from the crude crystallisate by chromatography on a hydroxypropylated dextran gel material in globular form (Sephadex® LH-20; column size: 6,000 ml; the crude product is taken up in methanol); after elution with a first fraction of 1,360 ml of methanol and further fractions each of 100 ml of methanol, it is recovered from fractions 6 to 10. M.p. 131°-132° after crystallisation from ethyl acetate and a small amount of methylene chloride.

Elemental analysis of the product, which contains half a mol of water, corresponds to the average empirical formula $C_{51}H_{98}N_6O_{22} \times 0.5$ mol $H_2O$: Found: C 52.80%; H 8.63%; N 7.44%; O 31.23%. Calculated: C 52.97%; H 8.63%; N 7.27%; O 31.13%.

The product is up to 25% soluble in water, up to 40% soluble in dimethyl sulfoxide, up to 10% soluble in methanol and up to 5% soluble in methylene chloride.

EXAMPLE 2

N-[ω-methoxy-(heptadecakis-ethyleneoxy)-carbonyl]-desferrioxamine B, in which heptadecakis-ethyleneoxy denotes a radical of the formula $-(CH_2-CH_2-O)_n-$ in which n has an average value of 17.

194.0 ml of trimethylchlorosilane are added at room temperature to a mixture of 86.5 g of desferrioxamine B-methanesulfonate in 2,000 ml of pyridine, the solution is stirred for 3 hours and then treated dropwise, within a period of 15 minutes, with an acylating reagent. The acylating reagent is prepared from 99.0 g (132 mmol) of a polyethylene glycol monomethyl ether having an average molecular weight of approximately 780 (Carbowax MPEG 750 of Messrs Union Carbide, which contains an average of 17 units of the formula $-CH_2-CH_2-O-$) in 1000 ml of toluene by treatment with 66.0 ml (132 mmol) of a 20% solution of phosgene in toluene, the solution being maintained at 70° for 3 hours. The reaction mixture is stirred for 16 hours at room temperature, then 2,000 ml of methanol are added and the whole is concentrated by evaporation. The residue, which still contains pyridine, is crystallised from approximately 500 ml of methylene chloride and 1,000 ml of diethyl ether and the product is dried for 16 hours under a high vacuum. The crude product is purified by chromatography on a hydroxypropylated dextran gel material in globular form (Sephadex® LH-20), the crude product being applied in methanol and eluted with methanol and the desired compound being obtained, after the first fraction of 1,590 ml and subsequent fractions each of 100 ml, from fractions 14 to 20. The residue is crystallised from ethyl acetate and diethyl ether, m.p. 125°-126° C.

Elemental analysis of the product, which contains one mol of water, corresponds to the average empirical formula $C_{61}H_{118}N_6O_{27} \times 1$ mol. $H_2O$: Found: C 53.17%; H 8.72%; N 5.80%; O 32.48%. Calculated: C 52.87%; H 8.72%; N 6.06%; O 32.33%.

The product is up to 40% soluble in water (viscous; up to 30% a clear solution), up to 45% soluble in dimethyl sulfoxide, up to 40% soluble in methanol and up to 20% soluble in methylene chloride.

EXAMPLE 3

N-[ω-methoxy-(dodecakis-ethyleneoxy)-carbonyl]-desferrioxamine B, in which dodecakis-ethyleneoxy denotes a radical of the formula —(CH$_2$—CH$_2$—O)$_n$— in which n has an average value of 12.

In a manner analogous to that described in Example 1, 6.56 g (10 mmol) of desferrioxamine B-methanesulfonate in 150 ml of pyridine are silylated with 15.5 ml (120 mmol) of trimethylchlorosilane and reacted with an acylating agent that is prepared as follows: 1.78 g (11 mmol) of 1,1'-carbonyl-bis-1H-imidazole is added to a solution of 5.5 g (10 mmol) of a polyethylene glycol monomethyl ether having an average molecular weight of approximately 560 (Carbowax MPEG 550 of Messrs Union Carbide, which has on average 12 units of the formula —CH$_2$—CH$_2$—O—) in 50 ml of toluene, and the whole is stirred at 70° C. for 1 hour and cooled. Working up in accordance with Example 1 yields the title compound, which corresponds to that of Example 1.

EXAMPLE 4

N-[ω-methoxy-(dodecakis-ethyleneoxy)-carbonylaminosulfonyl]-desferrioxamine B, in which dodecakis-ethyleneoxy denotes a radical of the formula —(CH$_2$—CH$_2$—O)$_n$— in which n has an average value of 12.

In an analogous manner to and with the same amounts of materials as in Example 3, desferrioxamine B-methanesulfonate is silylated and then reacted with an acylating reagent prepared in the following manner: 0.95 ml (11 mmol) of chlorosulfonylisocyanate is added to a solution of 5.5 g (10 mmol) of a polyethylene glycol monomethyl ether having an average molecular weight of approximately 560 (Carbowax MPEG 550 of Messrs Union Carbide, which has on average 12 units of the formula —CH$_2$—CH$_2$—O—) in 50 ml of toluene, and the whole is stirred at 70° C. for 1 hour and cooled. After the addition of 2000 ml of methanol the reaction mixture is concentrated to dryness. The residue, containing a substantial proportion of pyridine, is crystallised from approximately 500 ml of methylene chloride and 1000 ml of diethyl ether and dried for 16 hours under a high vacuum. A further purification by chromatography on a hydroxypropylated dextran gel material in globular form (Sephadex ® LH-20) may follow.

EXAMPLE 5

Dry ampoules containing 0.25 g of active ingredient for the preparation of 10% or 5% weight/volume (w/v) aqueous injection solutions with sterilised water are prepared by introducing 2.5 ml of a 10% (w/v) solution of the active ingredient into ampoules of 2.5 and 5 ml, respectively, and lyophilising in customary manner.

In an analogous manner, dry ampoules containing 0.5 g of active ingredient are prepared by filling 5.0 ml of a 10% (w/v) aqueous solution or 2.5 ml of a 20% (w/v) aqueous solution of the active component are filled into 5 ml and 2.5 ml ampoules, respectively, followed by lyophilization.

The solutions used for the lyophilisation may contain, in addition, for example, 8% (w/v) of mannitol, corresponding to 0.2 g or 0.4 g per ampoule, respectively.

The active ingredient used is one of the N-acylated desferrioxamine compounds described in the above and following Examples.

EXAMPLES 6

N-[ω-methoxy-(undecakis-ethyleneoxy)-carbonyl]-desferrioxamine B, in which undecakis-ethyleneoxy denotes a radical of the formula —(CH$_2$—CH$_2$—O)$_n$— in which n has an average value of 11.

A slightly turbid solution is obtained from a mixture of 446.0 g of desferrioxamine B-methanesulfonate in 4,000 ml of tetrahydrofuran and 1,000 ml of distilled water by heating at from 35° to 40° C.; 72.0 g of sodium carbonate are added to this solution which is stirred for 10 minutes.

142.4 g of 1,1'-carbonyl-bis-1H-imidazole are added to a mixture of 448.0 g of a polyethylene glycol monomethyl ether having an average molecular weight of approximately 516 (Carbowax MPEG 550, Messrs Union Carbide, the charge used being different from that of Example 1 and the polyethylene glycol containing on average 11 units of the formula —CH$_2$—CH$_2$—O—) in 2,000 ml of tetrahydrofuran, and the mixture is diluted with 200 ml of tetrahydrofuran and stirred for 16 hours. The resulting clear solution is added dropwise within a period of 30 minutes to the desferrioxamine mixture and, after 2 hours, the mixture is diluted with 1,000 ml of water, a clear solution forming in which after 5 hours it is no longer possible to detect desferrioxamine by high pressure liquid chromatography (HPLC). The whole is stirred for a further 16 hours at 0°, the organic solvent is evaporated off, and the aqueous portion is lyophilised.

The lyophilisate is taken up in 3,000 ml of methanol at 40°, and the mixture is stirred for 10 minutes, filtered, and rinsed with methanol. 6,000 ml of diisopropyl ether are added within a period of 75 minutes and at 20° to the clear filtrate, the resulting precipitate is filtered off, and the filtration residue is taken up in 2,200 ml of a 2:1 mixture of diisopropyl ether and methanol and stirred for 45 minutes. The resulting suspension cannot be filtered any further; it is concentrated by evaporation, taken up in 2,800 ml of methanol at from 50° to 60° C., filtered hot, and 6,000 ml of diisopropyl ether are added. After the whole has been cooled to 10° filtration is carried out and the filtration residue is washed with 1,000 ml of a 2:1 mixture of diisopropyl ether and methanol, dried and ground, then demineralised by chromatography on an adsorption resin of the polystyrene type (Amberlite ® XAD-1180), the product being applied in water and eluted with from 4:1 to 1:1 mixtures of water and isopropanol. Lyophilisation yields the product in the form of a white amorphous powder that contains half a mol of water of which the elemental analysis corresponds to the empirical formula C$_{49}$H$_{94}$N$_6$O$_{21}$×0.5 mol of H$_2$O:

Found: C 52.87%; H 8.55%; N 7.79%. Calculated: C 52.91%; H 8.61%; N 7.56%.

The product is up to 25% soluble in water, up to 40% soluble in dimethyl sulfoxide and 10% soluble in methanol.

EXAMPLE 7

N-[ω-methoxy-(undecakis-ethyleneoxy)-carbonyl]-desferrioxamine B, in which undecakis-ethyleneoxy denotes a radical of the formula —(CH$_2$—CH$_2$—O)$_n$— in which n has an average value of 11.

A mixture of 500.0 g of desferrioxamine B-methanesulfonate in 2,500 ml of distilled water changes into a clear solution after having been stirred for 10 minutes; this is cooled to 10° and 80 g of sodium carbonate in 500 ml of water are added thereto within a period of 5 minutes. Inoculation with free desferrioxamine B yields a viscous milky suspension which is filtered. The residue is washed with 500 ml of water and with 500 ml of a 1:1 mixture of water and acetone, then with portions, totalling 2,000 ml, of acetone, and dried for 16 hours at 40° under a pressure of approximately 20 mm/Hg and for a further 16 hours at 40° C. under a high vacuum.

A mixture of 381.0 g of the resulting desferrioxamine B in 4,000 ml of tetrahydrofuran and 2,000 ml of distilled water is added within a period of 30 minutes to the acylating agent, which is prepared as follows: 142.4 g of 1,1'-carbonyl-bis-1H-imidazole are added to a mixture of 448.0 g of a polyethylene glycol monomethyl ether having an average molecular weight of approximately 516 (Carbowax MPEG 550, Messrs Union Carbide, the charge used being different from that of Example 1 and the polyethylene glycol containing on average 11 units of the formula —$CH_2$—$CH_2$—O—) in 2,000 ml of tetrahydrofuran, 200 ml of tetrahydrofuran are added, and the whole is stirred for 16 hours and used as a clear solution.

The reaction mixture is stirred for 3 hours at from 40° to 45° C., and the clear solution is cooled and concentrated by evaporation in 4 portions. Each portion is twice treated with 1000 ml of n-butanol and concentrated to dryness by evaporation. The first two portions are combined, concentrated to a weight of 905 g and diluted with 345 g of n-butanol. The suspension is cooled to 10° C. and 18 ml of water are added; the whole is stirred for 16 hours and filtered. The filtration residue is washed with 1,000 ml of a 1:1 mixture of diisopropyl ether and n-butanol, taken up in 1,000 ml of butanol, stirred for 3 hours at from 40° to 45° C. and then for 16 hours at room temperature, and cooled to 10° C. The mixture is diluted with 5,000 ml of diisopropyl ether, 20 ml of water are added within a period of 2 hours and the whole is stirred for 16 hours at 10° C. and filtered. The filtration residue is washed with 1,000 ml of a 1:1 mixture of diisopropyl ether and n-butanol and dried at 40° C. under a high vacuum. The other two portions are worked up in an identical manner. The product contains 1 mol of water and the elemental analysis corresponds to the empirical formula $C_{49}H_{94}N_6O_{21} \times 1$ mol of $H_2O$:

Found: C 52.50%; H 8.50%; N 7.50%. Calculated: C 52.49%; H 8.63%; N 7.49%.

EXAMPLE 8

N-[ω-methoxy-(dodecakis-ethyleneoxy)-carbonyl]-O,O',O"-tri-(n-octanoyl)-desferrioxamine B, in which dodecakis-ethyleneoxy denotes a radical of the formula —($CH_2$—$CH_2$—O)$_n$— in which n has an average value of 12.

5.6 ml (40 mmol) of triethylamine and then, dropwise at room temperature, 11.99 ml (70 mmol) of caprylic acid chloride are added to a suspension of 11.47 g (10 mmol) of N-[ω-methoxy-(dodekakis-ethyleneoxy)-carbonyl]-desferrioxamine B, in which dodekakis-ethyleneoxy denotes a radical of the formula —($CH_2$—$CH_2$—O)$_n$— in which n has an average value of 12 (Example 1), in 100 ml of acetonitrile and 100 ml of methylene chloride. The slightly warmed reaction mixture is stirred for 16 hours at room temperature, a clear solution forming after 1 hour. The solvents are then evaporated, the residue is partitioned between methylene chloride and water, and the organic phase is dried over sodium sulfate and concentrated by evaporation under reduced pressure. The oily yellow product is purified by chromatography on silica gel, and is obtained in an amorphous, oily and colourless form. The strongly hygroscopic product contains half a mol of water and its elemental analysis corresponds to the empirical formula $C_{75}H_{140}N_6O_{25}$:

Found: C 58.74%; H 9.34%; N 5.43%; O 26.60%. Calculated: C 58.69%; H 9.26%; N 5.47%; O 26.58%.

In a thin layer chromatogram the product exhibits Rf values of 0.40 (9:1 mixture of methylene chloride and isopropanol) and 0.80 (4:1 mixture of methylene chloride and methanol).

EXAMPLE 9

N-[ω-methoxy-(dodecakis-ethyleneoxy)-carbonyl]O,-O',O"-tri-(ethoxycarbonyl)-desferrioxamine B, in which dodecakis-ethyleneoxy denotes a radical of the formula —($CH_2$—$CH_2$—O)$_n$— in which n has an average value of 12.

5.6 ml (40 mmol) of triethylamine and, dropwise at room temperature, 6.70 ml (70 mmol) of chloroformic acid ethyl ester are added to a suspension of 11.47 g (10 mmol) of N-[ω-methoxy-(dodekakis-ethyleneoxy)-carbonyl]-desferrioxamine B, in which dodekakis-ethyleneoxy denotes a radical of the formula —($CH_2$—$CH_2$—O)$_n$— in which n has an average value of 12 (Example 1), in 100 ml of acetonitrile and 100 ml of methylene chloride. The slightly warm mixture is stirred for 16 hours at room temperature, complete dissolution having occurred after 1 hour. The solvents are removed under reduced pressure, the residue is partitioned between methylene chloride and water, and the organic phase is dried over sodium sulfate and concentrated by evaporation. A total of 11.4 g of the oily yellow residue is chromatographed on 750 ml of silica gel (applied in methylene chloride, elution with a 95:5 mixture of methylene chloride/isopropanol), yielding an amorphous, oily and colourless product that is strongly hygroscopic and contains half a mol of water; its elemental analysis corresponds to the empirical formula: $C_{60}H_{110}N_6O_{28} \times 0.5$ mol $H_2O$:

Found: C 52.39%; H 8.28%; N 6.45%; O 33.44%. Calculated: C 52.51%; H 8.15%; N 6.12%; O 33.22%.

In a thin layer chromatogram the product exhibits Rf values of 0.20 (in a 9:1 mixture of methylene chloride and isopropanol) and 0.60 (in a 4:1 mixture of methylene chloride and methanol).

It is possible to obtain in an analogous manner N-[ω-methoxy-(dodecakis-ethyleneoxy)-carbonyl]-O,O',O"-tri-[ω-methoxy-(bis-or tris-ethyleneoxy)-carbonyl]-desferrioxamine B in which dodecakis-ethyleneoxy denotes a radical of the formula —(CH2—$CH_2$—O)n— in which n has an average value of 12.

EXAMPLE 10

N-[ω-methoxy-(dodecakis-ethyleneoxy)-carbonyl]-O,O',O"-tri-(ethoxycarbonylmethylaminocarbonyl)-desferrioxamine B, in which dodecakis-ethyleneoxy denotes a radical of the formula —($CH_2$—$CH_2$—O)$_n$— in which n has an average value of 12.

1.4 ml (10 mmol) of triethylamine and, dropwise at room temperature, 5.15 ml (70 mmol) of isocyanatoacetic acid ethyl ester are added to a suspension of 11.47 g (10 mmol) of N-[ω-methoxy-(dodekakis-ethyleneoxy)-carbonyl]-desferrioxamine B, in which dodekakis-ethyleneoxy denotes a radical of the formula —($CH_2$—$CH_2$—O)$_n$— in which n has an average value of 12 (Example 1), in 100 ml of acetonitrile and 100 ml of methylene chloride. The slightly warm reaction mixture is stirred for 4 hours at room temperature, complete dissolution having occurred after 1 hour. The solvents are removed under reduced pressure, the residue is partitioned between water and methylene chloride, and the organic phase is dried over sodium sulfate and concentrated by evaporation. A total of 13.4 g of the oily yellow residue is chromatographed on 750 ml of silica gel, the crude product being applied in methylene chloride and the desired material being eluted with a 95:5 mixture of methylene chloride and isopropanol. In this manner an amorphous, oily and colourless product that is strongly hygroscopic and contains half a mol of water is obtained. The elemental analysis corresponds to the empirical formula: $C_{66}H_{119}N_9O_{31} \times 1$ mol $H_2O$:

Found: C 50.96%; H 7.77%; N 8.63%; O 32.87%. Calculated: C 51.05%; H 7.85%; N 8.12%; O 32.97%.

In a thin layer chromatogram (silica gel) the product exhibits Rf values of 0.10 (in a 9:1 mixture of methylene chloride and isopropanol) and 0.75 (in a 4:1 mixture of methylene chloride and methanol).

EXAMPLE 11

Iron (III) complex of N-[ω-methoxy-(undecakis-ethyleneoxy)-carbonyl]-desferrioxamine B, in which undecakis-ethyleneoxy denotes a radical of the formula —$(CH_2—CH_2—O)_n$— in which n has an average value of 11.

A mixture of 300 g (300 mmol) of N-[ω-methoxy-(undecakis-ethyleneoxy)-carbonyl]-desferrioxamine B, in which undecakis-ethyleneoxy denotes a radical of the formula —$(CH_2—CH_2—O)_n$— in which n has an average value of 11 (Example 6) in 3,500 ml of water forms a solution after 10 minutes, to which, while stirring vigorously, 115 g (325 mmol) of iron(III) acetylacetonate in 2,000 ml of ethyl acetate are added; the reaction mixture is stirred vigorously for 2 hours at room temperature, then washed with a total of 15,000 ml of ethyl acetate. The aqueous phase is lyophilised and yields the desired iron(III) complex in the form of a deep red resinous product that is 25% soluble in dimethyl sulfoxide, 40% soluble in water (clear solution at 30%) 40% soluble in methanol and 30% soluble in methylene chloride, elemental analysis of which corresponds to the empirical formula $C_{49}H_{91}FeN_6O_{21}$:

Found: C 50.21%; H 7.99%; N 7.24%; Fe 4.90%. Calculated: C 50.12%; H 7.98%; N 7.16%; Fe 4.76%.

EXAMPLE 12

Iron(III) complex of N-[ω-methoxy-(heptadecakis-ethyleneoxy)-carbonyl]-desferrioxamine B, in which heptadecakis-ethyleneoxy denotes a radical of the formula —$(CH_2—CH_2—O)_n$— in which n has an average value of 17.

A solution of 8.5 g of iron(III) acetylacetonate in 400 ml of ethyl acetate is added to a solution of 27.3 g of N-[ω-methoxy-(heptadecakis-ethyleneoxy)-carbonyl]-desferrioxamine B, in which heptadecakis-ethyleneoxy denotes a radical of the formula —$(CH_2—CH_2—O)_n$— in which n has an average value of 17 (Example 2) in 400 ml of water and the reaction mixture is stirred well for 2 hours. Extraction is carried out with a total of 10,000 ml of ethyl acetate and the aqueous phase is lyophilised. The desired iron(III) complex is obtained in the form of a deep red resinous product and chromatographed on a hydroxypropylated dextran gel material in globular form (Sephadex ® LH 20), the crude product being applied in methanol and the pure substance being eluted with methanol. It is 1% soluble in dimethyl sulfoxide, 30% soluble in water, 40% soluble in methanol and 20% soluble in methylene chloride and its elemental analysis corresponds to the empirical formula $C_{61}H_{115}FeN_6O_{27}$:

Found: C 50.95%; H 8.23%; N 5.87%; Fe 3.97%. Calculated: C 50.93%; H 8.20%; N 5.84%; Fe 3.88%.

EXAMPLE 13

Gallium(III) complex of N-[ω-methoxy-(undecakis-ethyleneoxy)-carbonyl]-desferrioxamine B, in which undecakis-ethyleneoxy denotes a radical of the formula —$(CH_2—CH_2—O)_n$— in which n has an average value of 11.

A solution of 2.20 g (6 mmol) of gallium(III) acetylacetonate in 50 ml of ethyl acetate is added to a solution of 5.51 g of N-[ω-methoxy-(undecakis-ethyleneoxy)-carbonyl]-desferrioxamine B, in which undecakis-ethyleneoxy denotes a radical of the formula —$(CH_2—CH_2—O)_n$— in which n has an average value of 11 (Example 6) in 50 ml of water while stirring vigorously and the reaction mixture is stirred vigorously for one hour at room temperature. Extraction is carried out a few times with a large amount of ethyl acetate, and the aqueous phase is lyophilised. In this manner the desired gallium(III) complex is obtained in the form of a colourless amorphous resin which is 30% soluble in water and 20% soluble in dimethyl sulfoxide. The elemental analysis corresponds to the average empirical formula $C_{49}H_{91}GaN_6O_{21}$:

Found: C 50.12%; H 7.80%; N 7.20%. Calculated: C 50.30%; H 7.84%; N 7.18%.

EXAMPLE 14

Indium(III) complex of N-[ω-methoxy-(undecakis-ethyleneoxy)-carbonyl]-desferrioxamine B, in which undecakis-ethyleneoxy denotes a radical of the formula —$(CH_2—CH_2—O)_n$— in which n has an average value of 11.

A solution of 2.47 g (6 mmol) of indium(III) acetylacetonate in 50 ml of ethyl acetate is added to a solution of 5.51 g (5 mmol) of N-[ω-methoxy-(undecakis-ethyleneoxy)-carbonyl]-desferrioxamine B, in which undecakis-ethyleneoxy denotes a radical of the formula —$(CH_2—CH_2—O)_n$— in which n has an average value of 11 (Example 6) in 50 ml of water while stirring vigorously and the reaction mixture is further stirred for one hour. The aqueous phase is washed with a large amount of ethyl acetate and then lyophilised. The desired indium complex is obtained in the form of a white amorphous resin which is 30% soluble in water and 20% soluble in dimethyl sulfoxide. The elemental analysis corresponds to the average empirical formula $C_{49}H_{91}InN_6O_{21}$:

Found: C 47.50%; H 7.50%; N 6.80%. Calculated: C 47.73%; H 7.60%; N 6.82%.

EXAMPLE 15

Manganese(III) complex of N-[ω-methoxy-(undecakis-ethyleneoxy)-carbonyl]-desferrioxamine B, in which undecakis-ethyleneoxy denotes a radical of the formula —$(CH_2—CH_2—O)_n$— in which n has an average value of 11.

A solution of 31.7 g (90 mmol) of manganese(III) acetylacetonate in 700 ml of ethyl acetate is added to a mixture of 88.26 g (80 mmol) of N-[ω-methoxy-(undecakis-ethyleneoxy)-carbonyl]-desferrioxamine B, in which undecakis-ethyleneoxy denotes a radical of the formula —$(CH_2—CH_2—O)_n$— in which n has an average value of 11 (Example 6) and 700 ml of water while stirring vigorously and the whole is stirred for one hour at room temperature. The aqueous phase is washed with a large amount of ethyl acetate and then lyophilised. The desired manganese complex is obtained in the form of a deep green resinous product which is up to 40% soluble in water, 25% soluble in dimethyl sulfoxide, 40% soluble in methanol and 30% soluble in methylene chloride. The elemental analysis corresponds to the average empirical formula $C_{49}H_{91}MnN_6O_{21}$:

Found: C 50.60%; H 7.90%; N 7.22%; Mn 5.05%.
Calculated: C 50.55%; H 7.96%; N 7.22%; Mn 4.72%.

EXAMPLE 16

Iron(III) complex of N-[ω-methoxy-(undecakis-ethyleneoxy)-carbonyl]-desferrioxamine B, in which undecakis-ethyleneoxy denotes a radical of the formula $-(CH_2-CH_2-O)_n-$ in which n has an average value of 11.

A total of 27.03 g (100 mmol) of iron(III) chloride is added at 15 minute intervals, in 10 portions each of 2.70 g, to a solution, which forms within a period of 10 minutes, of 11.03 g (10 mmol) of N-[ω-methoxy-(undecakis-ethyleneoxy)-carbonyl]-desferrioxamine B, in which undecakis-ethyleneoxy denotes a radical of the formula $-(CH_2-CH_2-O)_n-$ in which n has an average value of 11 (Example 6) in 500 ml of deionised water. After about 2½ hours, it is no longer possible to detect any starting material by high pressure liquid chromatography. The reaction product is adjusted to pH 7.5 by the addition of aqueous sodium hydroxide, and then lyophilised. The lyophilisate is dissolved in methanol and purified with the aid of a hydroxypropylated dextran gel material in globular form (Sephadex ® LH-20). The dark red fractions washed out with methanol contain the desired iron(III) complex, the elemental analysis of which corresponds to the average empirical formula $C_{49}H_{91}FeN_6O_{21} \times 1$ mol $H_2O$:

Found: C 50.21%; H 7.99%; N 7.24%; Fe 4.90%.
Calculated: C 50.12%; H 7.98%; N 7.16%; Fe 4.76%.

The product is up to 25% soluble in dimethyl sulfoxide, up to 40% soluble in water (viscous solution; clear solution up to 30%), 40% soluble in methanol and 30% soluble in methylene chloride.

What is claimed is:

1. A compound of the formula

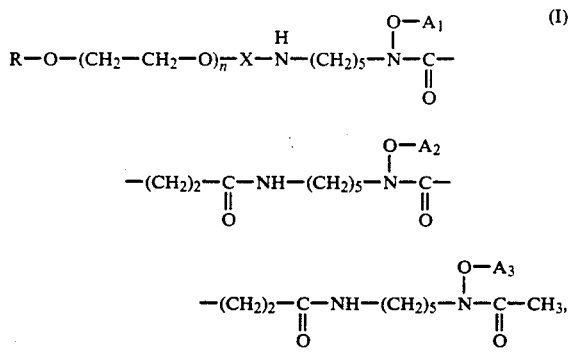

in which R is an alkyl having up to 4 carbon atoms, n has an verage value of at least 9, X is a radical of the formula $-C(=O)-(NH-SO_2)_m-$ in which m is 0 or 1 and, if m is 1, the carbonyl group may be bonded to the oxygen atom or to the nitrogen atom, and each of the radicals $A_1$, $A_2$ and $A_3$ has the same meaning and is hydrogen, or alkanoyl or alkenoyl each having upto and including 20 carbon atoms, alkoxycarbonyl having up to and including 20 carbon atoms in the alkyl moiety, oxaalkoxycarbonyl having up to and including 20 carbon atoms in the alkyl moiety and wherein up to and including methylene groups are replaced by oxygen atoms and in each case two carbon atoms separate the oxygen atoms from one another, alkylaminocarbonyl having up to and including 20 carbon atoms in the alkyl moiety, or substituted alkylaminocarconyl having up to and including 20 carbon atoms in the alkyl moiety and being substituted bycarboxy, lower alkoxycarbonyl having up to and including 4 carbon atoms in the lower alkyl moiety, carbamoyl and/or amino, hydroxy, mercapto, lower alkylthio having up to and including 4 carbon atoms, phenyl, or by hydroxyphenyl, or a pharmaceutically acceptable salt of a salt forming compound of formula I.

2. A compound of formula I according to claim 1 in which R is methyl, X has the meaning given in claim 1 and m is 0, n has an average value of from approximately 10 to approximately 17, and each of the radicals $A_1$, $A_2$ and $A_3$ is hydrogen.

3. A compound according to claim 1 and being N-[ω-methoxy-(dodecakis-ethyleneoxy)-carbonyl]-desferrioxamine B, in which dodecakis-ethyleneoxy denotes a radical of the formula $-(CH_2-CH_2-O)_n-$ in which n has an average value of 12.

4. A compound according to claim 1 and being N-[ω-methoxy-(heptadecakis-ethyleneoxy)-carbonyl]-desferrioxamine B, in which heptadecakis-ethyleneoxy denotes a radical of the formula $-(CH_2-CH_2-O)_n-$ in which n has an average value of 17.

5. A compound according to claim 1 and being N-[ω-methoxy-(undecakis-ethyleneoxy)-carbonyl]-desferrioxamine B, in which undecakis-ethyleneoxy denotes a radical of the formula $-(CH_2-CH_2-O)_n-$ in which n has an average value of 11.

6. A compound according to claim 1 and being N-[ω-methoxy-(dodecakis-ethyleneoxy)-carbonyl]-O,O',O''-tri-(n-octanoyl)-desferrioxamine B, in which dodecakis-ethyleneoxy denotes a radical of the formula $-(CH_2-CH_2-O)_n-$ in which n has an average value of 12.

7. A compound according to claim 1 and being N-[ω-methoxy-(dodecakis-ethyleneoxy)-carbonyl]-O,O',O''-tri-(ethoxycarbonyl)-desferrioxamine B, in which dodecakis-ethyleneoxy denotes a radical of the formula $-(CH_2-CH_2-O)_n-$ in which n has an average value of 12.

8. A compound according to claim 1 and being N-[ω-methoxy-(dodecakis-ethyleneoxy)-carbonyl]-O,O',O''-tri-(ethoxycarbonylmethylaminocarbonyl)-desferrioxamine B, in which dodecakis-ethyleneoxy denotes a radical of the formula $-(CH_2-CH_2-O)_n-$ in which n has an average value of 12.

9. A compound of formula I according to claim 1 in which n has an average value of from approximately 10 to approximately 17, or a pharmaceutically acceptable salt of such a compound having salt forming properties.

10. A compound of formula I according to claim 1 in which m is 0, n has an average value of from approximately 10 to approximately 17, and each of the radicals $A_1$, $A_2$ and $A_3$, has the same meaning and are hydrogen, alkanoyl having up to and including 12 carbon atoms, alkoxycarbonyl having up to and including 7 carbon atoms in the alkyl group, oxaalkoxycarbonyl having up to and including 7 carbon atoms in the alkyl group wherein one or two methylene groups are replaced by oxygen atoms and oxygen atoms are separated from each other by two carbon atoms, or alkylaminocarbonyl having up to and including 7 carbon atoms in the alkyl group and which is unsubstituted or is substituted in the 1- or 2- position by an alkoxycarbonyl which itself has up to and including 4 carbon atoms in the alkyl portion.

11. A trivalent metal ion scavenger pharmaceutical composition comprising a trivalent metal ion scavenging effective amount of a compound of claim 1 so as to increase excretion of trivalent metal ions from a mammal to which it is administered and a pharmaceutically acceptable carrier therefor.

* * * * *